United States Patent [19]

Nichols et al.

[11] Patent Number: 5,723,764
[45] Date of Patent: Mar. 3, 1998

[54] CELLULOSE SYNTHESIS IN THE STORAGE TISSUE OF TRANSGENIC PLANTS

[75] Inventors: Scott Edward Nichols, Johnston; George William Singletary, Ankeny, both of Iowa

[73] Assignee: Pioneer Hi-Bred International, Inc., Des Moines, Iowa

[21] Appl. No.: 475,928

[22] Filed: Jun. 7, 1995

[51] Int. Cl.$^6$ .................. C12N 15/29; C12N 15/31; C12N 15/82; A01H 5/00
[52] U.S. Cl. .................. 800/205; 800/DIG. 55; 800/DIG. 56; 800/DIG. 58; 800/DIG. 42; 536/23.7; 536/24.1; 435/172.3
[58] Field of Search .................. 800/205, DIG. 55, 800/DIG. 56, DIG. 58, DIG. 42; 536/23.7, 24.1; 435/172.3

[56] References Cited

U.S. PATENT DOCUMENTS

| | | | |
|---|---|---|---|
| 4,956,282 | 9/1990 | Goodman et al. | 435/69.51 |
| 5,268,274 | 12/1993 | Ben-Bassat et al. | 435/69.1 |
| 5,349,123 | 9/1994 | Shewmaker et al. | 800/205 |

OTHER PUBLICATIONS

Ross, et al. "Cellulose Biosynthesis and Function in Bacteria" *Microbiol. Rev.*; vol. 55(1); pp. 35–58; (1991).

Saxena, et al. "Characterization of Genes in the Cellulose-Synthesizing Operon (acs Operon) of *Acetobacter xylinum*: Implications for Cellulose Crystallization" *J. Bacteriol.*; vol. 176(18); pp. 5735–5752; (1994).

Lin, et al. "Identification of the Uridine 5'-Diphosphoglucose (UDP-Glc) Binding Subunit of Cellulose Synthase in *Acetobacter xylinum* Using the Photoaffinity Probe 5-Azido-UDP-Glc" *J. Biol. Chem.*; vol. 265(9); pp. 4782–4784; (1990).

Creech, "Carbohydrate Synthesis in Maize" *Advances in Agronomy*; vol. 20, pp. 275–322; (1968).

Müller-Röber, et al. "Inhibition of the ADP-Glucose Pyrophosphorylase in Transgenic Potatoes Leads to Sugar-Storing Tubers and Influences Tuber Formation and Expression of Tuber Storage Protein Genes" *The Embo Journal*; vol. 11(4); 1229–1238; (1992).

Utsumi, et al. "Expression and Accumulation of Normal and Modified SoybeanGlycinins in Potato Tubers" *Plant Science*; vol. 102(2); pp. 181–188; (1994).

Visser, et al. "Transformation of Homozygous Diploid Potatoe with an *Agrobacterium tumefaciens* Binary Vector System by Adventitous Shoot Regeneration on Leaf and Stem Segments" *Plant Molecular Biology*; vol. 12; pp. 329–337; (1989).

Ebskamp, et al. "Accumulation of Fructose Polymers in Transgenic Tobacco" *Bio/Technology*; vol. 12; pp. 272–275; (1994).

Armstrong, et al. "Regeneration of Plants from Somatic Cell Cultures: Applications for in vitro Genetic Manipulation" *The Maize Handbook*; Freeling, et al. eds. pp. 663–671; (1994).

Amor et al. The Plant Cell. vol. 3, 989–995. Sep. 1991. Evidence for a Cyclic Diguanylate Acid-Dependent Cellulose Synthase in Plants. Sep. 1991.

*Primary Examiner*—Douglas W. Robinson
*Assistant Examiner*—Thomas Haas

[57] ABSTRACT

The present invention provides methods of synthesizing cellulose in the storage tissue of transgenic plants by introducing the cellulose biosynthetic enzymes into the storage tissue. Specifically, the present invention involves introducing the genes for cellulose biosynthesis from the species *Acetobacter xylinium* into a given plant under the control of storage tissue specific promoters.

21 Claims, No Drawings

CELLULOSE SYNTHESIS IN THE STORAGE TISSUE OF TRANSGENIC PLANTS

FIELD OF THE INVENTION

The present invention relates to the field of cellulose production. Specifically, the present invention relates to the synthesis of cellulose in the storage tissue of transgenic plants.

BACKGROUND OF THE INVENTION

Cellulose is a β(1–4) linked linear glucan synthesized by bacteria, fungi and plants. In all three cases, synthesis occurs at the plasma membrane by membrane-bound enzyme systems.

The cell wall is a tough, meshlike network wherein cellulose fibrils are primary architectural elements. The plant cell wall is a semipermeable composite tissue of high species variability and is compounded from layered deposits of cellulose fibrils in which are embedded more amorphous polymers, including neutral and acidic polysaccharides, glycoproteins, and waxy aromatic substances. In analogies inspired by electron-microscopic images of plant cell wall replicas, the structural role of cellulose has been likened to that of the nylon strands of fiber glass or to the supporting rods within reinforced concrete. Cellulose fibrils are highly insoluble and inelastic and, because of their molecular configuration, have a tensile strength comparable to that of steel. Consequently, cellulose imparts a unique combination of chemical resilience, mechanical support and flexibility to the tissues in which it resides. These qualities are readily apparent in such common plant products as paper, lumber, and cotton textiles.

Cellulose has a variety of industrial uses. It is widely used in the paper and food industry, as well as in the oil and other drilling processes as a lubricant. Cellulose can also serve as a substrate for modifications such as carboxy methylation; methyl, ethyl and propyl ether formation, etc.

The ever-increasing demands of industrialization have imposed extreme negative pressures on the delicate ecological balance of our planet. Because forests are in particular jeopardy at present, there have been efforts to develop alternatives to the harvesting of forests for the acquisition of materials conventionally derived from trees. Examples of the development of such alternatives include the case of bacteria that produce the fibrous polymer cellulose.

In sheer bulk, cellulose is the most abundant organic macromolecule on earth, where it occupies a great reservoir of the carbon cycle; in higher plants, its biogenesis is an integral event in cell growth and development. Currently, cellulose is isolated from natural sources and also produced by fermentation. The former is more widely used and typically involves extraction from wood as wood pulp. Cellulose thus isolated is used to generate fiber for paper manufacturing, food uses and as substrates for subsequent modifications (via esterified or etherified adducts). This process, utilizing wood chips as the starting material, is unsatisfactory because it uses a non-annually renewable source.

A less common method of manufacturing cellulose is a fermentation process utilizing bacteria that produce cellulose. In bacteria, most notably Acetobacter sp., the cellulose is secreted to the medium and can be isolated by extensive washing to remove the cells, cellular debris and medium. See e.g. Ross, et al., "Cellulose Biosynthesis and function in Bacteria." *Microbiol. Rev.*; Vol. 55(1); pp. 35–58; (1991); incorporated herein in its entirety by reference. This method is not popular because it involves a large capital outlay in running a fermentation facility, treating waste products and operating input costs. A third way to produce cellulose is isolation from algae and non-woody plant tissue.

Based on the foregoing there exists a need to produce cellulose in an economically feasible way, using annually-renewable sources, with an economically acceptable concentration of cellulosic material.

It is therefore an object of the present invention to provide environmentally friendly methods of producing cellulose from annually-renewable sources.

It is a still further object of the present invention to provide inexpensive methods of producing cellulose that do not require a large capital outlay and prohibitive operating costs.

SUMMARY OF THE INVENTION

The present invention involves the production of cellulose in the storage tissue of a transgenic plant by introducing the cellulose biosynthetic enzymes into the storage tissue. This provides a plentiful, cheaply produced, easily purified and easily harvestable source of cellulose with economically-acceptable initial concentrations of cellulose.

Specifically, the present invention involves introducing the genes for cellulose synthesis from the species *Acetobacter xylinium* into a given plant under the control of storage tissue specific promoters.

DETAILED DESCRIPTION OF THE INVENTION

As used herein, "storage tissue" means tissues where metabolic reserves are stored, including but not limited to roots, tubers and grain. For example, in maize, the storage tissue would include the endosperm and scutellum; in cassava, the root; and in potato, the tubers.

As used herein, "vacuole" means the cellular compartment bounded by the tonoplast membrane.

As used herein, "cellulose synthase complex" means the cellulose synthesizing enzyme whose peptides are the gene products of acs.

Cellulose synthesis in the endosperm of a transgenic plant occurs by formation of β(1–4) linkages made by cellulose synthase which utilizes UDP-glucose as a substrate. Furthermore, cyclic-di-GMP is a required allosteric modifier for cellulose synthase. See e.g. Ross, et al., cited hereinabove. Genes for cellulose synthase production are well known and come from the operon acs. The genes involved include acsA, acsB and acsC. The operon has been well characterized. See e.g. Saxena et al., *J. Bacteriol.* Vol. 176 (18); pp. 5735–5752; (1994) incorporated herein in its entirety by reference. The products of the above genes are also well known to those skilled in the art. See e.g. Lin, et al., (1990); "Identification of the Uridine 5'-Diphosphoglucose (UDP-Glc) Bindings Subunit of Cellulose Synthase in *Acetobacter xylinum* Using the Photoaffinity Probe 5-Azido-UDP-Glc." *J. of Biol. Chem.*; Vol. 265(9); pp. 4782–4784; (1990); incorporated herein in its entirety by reference. The synthase genes are all engineered to remove their native signal sequences and subsequently engineered with amyloplast targeting sequences and/or vacuole targeting sequences.

Additionally, the diguanylate cyclase enzyme are also introduced into the transgenic plant. This is a two polypeptide enzyme, as disclosed in Ross, et al., cited hereinabove, and is cloned using standard techniques. The peptides are sequenced, after the protein is purified, and are reverse translated to generate oligonucleotides to screen a library using standard techniques. Of the five genes introduced into the transgenic plant, the three comprising cellulose synthase are engineered such that they are targeted to the amyloplast and/or vacuole. The two involving diguanylate cyclase are not targeted and remain in the cytosol.

The cellulose is preferably produced in a transgenic plant selected from the group consisting of maize, potato, cassava, sweet potato, rye, barley, wheat, sorghum, oats, millet, sugarcane, triticale and rice, according to the present invention. More preferably, the cellulose is produced in a transgenic plant selected from the group consisting of maize, potato, cassava, sugarcane and sweet potato. Even more preferably, the cellulose is produced in maize or potato. Most preferably, the cellulose is produced in maize.

In a highly preferred embodiment of the present invention, transformation occurs in maize of genotypes $sh_2$, $bt_2$, or $bt_1$ mutants wherein starch biosynthesis is greatly diminished. Thus, a greater proportion of monomer or assimilate is available to be synthesized into $\beta(1-4)$ polymers. See e.g. Creech, "Carbohydrate Synthesis in Maize," Advances in Agronomy, Vol. 20, pp. 275-322 (1968); incorporated herein in its entirety by reference. Also highly preferred are mutants which have been genetically engineered to abolish starch biosynthesis. See e.g. Müller-R ober, et al., "Inhibition of the ADP-glucose Pyrophosphorylase in Transgenic Potatoes Leads to Sugar-Storing Tubers and Influences Tuber Formation and Expression of Tuber Storage Protein Gene," *The Embo Journal*, Vol. 11(4), pp. 1229-1238; (1992); incorporated herein in its entirety by reference.

The generation of plants that produce cellulose is achieved by transformation methods that are well known in the art, and thus constitute no part of this invention. The cellulose is synthesized by insertion of an expression cassette containing an aforementioned synthetic gene which, when transcribed and translated, works with the other four genes to yield the desired cellulose. Such empty expression cassettes, providing appropriate regulatory sequences for plant expression of the desired sequence, are also well-known, and the nucleotide sequence for the synthetic gene, either RNA or DNA, can readily be derived from the amino acid sequence for the protein using standard texts and the references provided. The above-mentioned synthetic genes preferably employ plant-preferred codons to enhance expression of the desired protein.

The genes which code for the present proteins can be inserted into an appropriate expression cassette and introduced into cells of a plant species. Thus, an especially preferred embodiment of this method involves inserting into the genome of the plant a DNA sequence coding for a present protein in proper reading frame, together with transcription promoter and initiator sequences active in the plant. Transcription and translation of the DNA sequence under control of the regulatory sequences causes expression of the protein sequence at levels which provide an elevated amount of the protein in the tissues of the plant. Synthetic DNA sequences can then be prepared which code for the appropriate sequence of amino acids, and this synthetic DNA sequence can be inserted into an appropriate plant expression cassette.

Numerous plant expression cassettes and vectors are well known in the art. By the term "expression cassette" is meant a complete set of control sequences including promoter, initiator, and termination sequence which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence.

By the term "vector" herein is meant a DNA sequence which is able to replicate and express a foreign gene in a host cell. Typically, the vector used has one or more restriction endonuclease recognition sites which may be cut in a predictable fashion by use of the appropriate enzymes such vectors are preferably constructed to include additional structural gene sequences imparting antibiotic or herbicide resistance, which then serve as markers to identify and separate transformed from nontransformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, both genomic DNA and cDNA encoding a gene of interest may be used in this invention. The vector of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

The expression cassette comprising the structural gene for a protein involved in this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli*, *S. typhimurium*, and *Serratia marcescens*. Eukaryotic hosts such as yeast or filamentous fungi may also be used in this invention. Since these hosts are also microorganisms, it will be essential to ensure that plant promoters which do not cause expression of the protein in bacteria are used in the vector.

The isolated cloning vector will then be introduced into the plant cell using any convenient technique, including electroporation (in protoplasts), retroviruses, bombardment, and microinjection into cells from monocotyledonous or dicotyledonous plants in cell or tissue culture to provide transformed plant cells containing as foreign DNA at least one copy of the DNA sequence of the plant expression cassette. Preferably, the monocotyledonous species will be selected from maize, sugarcane, sorghum, wheat or rice, and the dicotyledonous species will be selected from potato, cassava and sweet potato. Using known techniques, protoplasts can be regenerated and cell or tissue culture can be regenerated to form whole fertile plants which carry and express the gene for a protein involved in this invention. Accordingly, a highly preferred embodiment of the present invention is a transformed maize plant, the cells of which contain as foreign DNA at least one copy of the DNA sequence of an expression cassette of the protein.

It will also be appreciated by those of ordinary skill that the plant vectors provided herein can be incorporated into *Agrobacterium tumefaciens*, which can then be used to transfer the vector into susceptible plant cells, primarily from dicotyledonous species. Thus, this invention provides a method for introducing the protein in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention.

For example, the potato plant can be transformed via *Agrobacterium tumefaciens* to produce the cellulose. The transformation cassette comprises a patatin promoter, followed by the protein coding sequence and the neomycin phosphotransferase polyadenylation site/terminator. See e.g. Utsumi, et al., "Expression and Accumulation for Normal and Modified Soybean Glycinins in Potato Tubers," *Plant Science;* Vol. 102(2); pp. 181–188; (1994) (Limerick); incorporated herein in its entirety by reference. The transgenic cassette is placed into a transformation vector. For example, BIN19, or derivatives thereof, are useful when transforming via *Agrobacterium tumefaciens*. See e.g. Visser, et al., "Transformation of Homozygous Diploid Potato with an Agrobacterium-tumefaciens Binary Vector System by Adventitious Shoot Regeneration on Leaf and Stem Segments," *Plant Mol. Biol.;* Vol. 12(3); pp. 329–338; (1989); incorporated herein in its entirety by reference.

For maize transformation vectors, the promoters include any promoter whose expression is specific and limited to endosperm cells. Included are those encodin either 22 kDa zein, opaque2, gamma zein and waxy. These lead into the gene and are followed by the endogenous terminator or the heterogeneous PINII terminator.

The gene is directed to the maize endosperm amyloplast using a suitable transit sequence. Transit sequences useful in directing the enzyme into the amyloplast for accumulation within the amyloplast include but are not limited to ribulose biphosphate carboxylase small subunit, brittle-1, waxy, and chlorophyll AB binding protein. The transit sequences are juxtaposed between the promoter and the protein coding sequence and fused in translational reading frame with the protein moiety.

Standard methods are also used to direct the enzyme into the vacuole. For vacuolar signal sequences, see e.g. Ebskamp, et al., "Accumulation of Fructose Polymers in Transgenic Tobacco," *Bio/technology;* Vol. 12; pp. 272–275; (1994); incorporated herein in its entirety by reference.

For maize transformation and regeneration see e.g. Armstrong, C., "Regeneration of Plants from Somatic Cell Cultures: Applications for in vitro Genetic Manipulation," *The Maize Handbook*, Freeling, et al. eds, pp. 663–671, (1994); incorporated herein in its entirety by reference.

Once a given plant is transformed, the cellulose produced can be isolated, by standard methods, known to one skilled in the art. The cellulose thus obtained in the transgenic plant can be substituted for a variety of uses as mentioned hereinbefore.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What is claimed is:

1. A method of manufacturing cellulose in the storage tissues of transgenic plants comprising: stably transforming the plant with genes encoding the cellulose synthase complex and diguanylate cyclase, wherein said cellulose synthase complex genes and said diguanylate cyclase genes are derived from *Acetobacter xylinium*, wherein said cellulose synthase complex genes are expressible in the storage tissues of said transgenic plant; and growing the plant under conditions suitable for expression of said synthase and cyclase genes and the synthesis of cellulose thereby.

2. The method of claim 1 wherein the cellulose synthase complex comprises the three cellulose synthase genes acsA, acsB, and acsC.

3. The method of claim 2 wherein the products of the cellulose synthase complex genes are targeted to the amyloplast or vacuole of the transgenic plant.

4. The method of claim 1 wherein the products of the diguanylate cyclase genes are directed to the cytosol of the transgenic plant.

5. The method of claim 4 wherein the transgenic plant is selected from the group consisting of maize, potato, cassava, sweet potato, rye, barley, wheat, sorghum, oats, sugarcane, millet, triticale and rice.

6. The method of claim 5 wherein the cellulose is produced in the amyloplast of the transgenic plant.

7. The method of claim 6 wherein the transformation is performed using a transit sequence selected from the group consisting of ribulose biphosphate carboxylase, small subunit; waxy; brittle-1 and chlorophyll AB binding protein.

8. The method of claim 7 wherein the cellulose is produced in maize.

9. The method of claim 8 wherein the transformation involves a promoter selected from the group consisting of 22 kDa zein, opaque2, gamma zein and waxy.

10. A transgenic plant wherein cellulose is produced in the storage tissues of said plant due to the activity of one or more transgenes derived from *Acetobacter xylinium*.

11. The plant of claim 10 wherein the plant is selected from the group consisting of maize, potato, cassava, sweet potato, sugarcane, rye, barley, wheat, sorghum, oats, millet, triticale and rice.

12. The plant of claim 11 wherein the cellulose is synthesized by stably transforming the plant with genes encoding the cellulose synthase complex complex and diguanylate cyclase, wherein said cellulose synthase complex genes are expressible in the storage tissues of said transgenic plant.

13. The plant of claim 12 wherein the cellulose synthase complex comprises the three cellulose synthase genes, acsA, acsB and acsC.

14. The plant of claim 13 wherein the cellulose synthase genes are targeted to the amyloplast or vacuole of the transgenic plant.

15. The plant of claim 14 wherein diguanylate cyclase enzyme genes are directed to the cytosol of the transgenic plant.

16. The plant of claim 15 wherein the plant is selected from the group consisting of maize, potato, cassava, sugarcane and sweet potato.

17. The plant of claim 16 wherein the plant has been genetically engineered to diminish or abolish starch biosynthesis.

18. The plant of claim 17 wherein the plant is maize.

19. The plant of claim 18 wherein the plant is selected from the group of maize mutant genotypes consisting of $sh_2$, $bt_2$ and $bt_1$.

20. The plant of claim 19 wherein the cellulose synthase genes are targeted to the maize endosperm amyloplast using a transit sequence selected from the group consisting of brittle-1, ribulose biophosphate carboxylase small subunit and waxy.

21. The method of claim 1 including the further step of isolating the cellulose so produced.

* * * * *